United States Patent [19]
Fogarty

[11] 3,993,076
[45] Nov. 23, 1976

[54] VESSEL OCCLUDING INSTRUMENT
[76] Inventor: Thomas J. Fogarty, 770 Welch Road, Palo Alto, Calif. 94304
[22] Filed: Apr. 21, 1975
[21] Appl. No.: 569,907

Related U.S. Application Data
[63] Continuation-in-part of Ser. No. 389,922, Aug. 20, 1973, Pat. No. 3,880,166.

[52] U.S. Cl. .................................. 128/325; 128/327
[51] Int. Cl.$^2$ ......................................... A61B 17/12
[58] Field of Search .......... 128/325, 327, 346, 326, 128/335.5

[56] References Cited
UNITED STATES PATENTS

| | | | |
|---|---|---|---|
| 1,252,260 | 1/1918 | Gilberg | 128/327 |
| 2,803,253 | 8/1957 | Campbell | 128/327 |
| 2,936,759 | 5/1960 | Yuhas | 128/327 |
| 3,762,418 | 10/1973 | Wasson | 128/335.5 |
| 3,880,166 | 4/1975 | Fogarty | 128/325 |
| 3,910,280 | 10/1975 | Talonn | 128/327 |

Primary Examiner—Aldrich F. Medbery
Attorney, Agent, or Firm—Wills, Green & Mueth Law Corporation

[57] ABSTRACT

An instrument for atraumatic occlusion of small blood vessels, which includes an elongated body member with opposed ends and top and bottom faces and having one end thereof fastened adjacent the center of a length of resilient surgical tape, the other end of the body member being constructed and arranged to receive and releasably maintain one end of said tape in a selected adjusted position to entrap and occlude a blood vessel between the bottom face of the body member and said one end of the tape. In the preferred form, the bottom face comprises a large, resilient pad and said face forms an obtuse angle with the length of tape when the latter is in an extended position.

10 Claims, 8 Drawing Figures

VESSEL OCCLUDING INSTRUMENT

CROSS-REFERENCE TO RELATED APPLICATION

This application is a continuation-in-part application of Ser. No. 389,922, filed Aug. 20, 1973 and now U.S. Pat. No. 3,880,166.

BACKGROUND AND BRIEF SUMMARY OF THE INVENTION

The present invention relates generally to the surgical field, and more particularly to a novel blood vessel occluding instrument which provides for atraumatic occlusion of blood vessels without using large cumbersome clamps or clips. It is particularly useful for smaller vessels.

The necessity for an atraumatic means of occluding small vessels has greatly increased with the advent of coronary artery surgery. The anatomy, location and fragile nature of the coronary vessels precludes the use of conventional instruments such as clamps and clips for the routine occlusion of such vessels.

To obtain a secure anastomosis, the periarterial tissue must be left in place. Accordingly, the dissection of an artery in order to obtain a sufficient length of the artery to apply a conventional occluding device such as a clamp, significantly increases the technical difficulty of obtain a secure anastomosis.

It is an object of the present invention, therefore, to provide a novel vessel occluding instrument for the atraumatic occlusion of small vessels, which is light in weight, of low profile, and which causes no distortion of the vessel.

Another object is to provide such an instrument which is relatively simple in construction and which can be produced in large quantities at a relatively low cost.

A further object is to provide such a novel occluding instrument which provides for the occlusion of an artery in an anterior posterior direction without significant distortion of an arterial wall except at two points.

Yet another object is to provide a vessel occluding instrument in which the vessel is entrapped and occluded between two resilient surfaces, one of which is relatively large compared to the other, whereby the trauma usually associated with unyielding materials is significantly diminished.

An additional object is to provide such a vessel occluding instrument which includes means for manipulating vessels, as by pulling them from side to side or elevating them in order to obtain an unobstructed view of the vessel and without the necessity of pinching the structure between the fingers. More particularly, it is an object to provide such an instrument in which the aforementioned resilient surface forms an obtuse angle with the surgical tape to facilitate such manipulations.

I have discovered that the above objects and advantages are achieved by a vessel occluding instrument which includes a rigid body member which has two lengths of resilient tape extending from the surfaces thereof adjacent one end, a resilient pad in engagement with the bottom surface, and a slot at the other end of the body member for receiving and releasably holding one length of said tape in a selected adjusted position to occlude a vessel between the pad and said length of tape.

DESCRIPTION OF THE PREFERRED EMBODIMENTS

Figure 1:
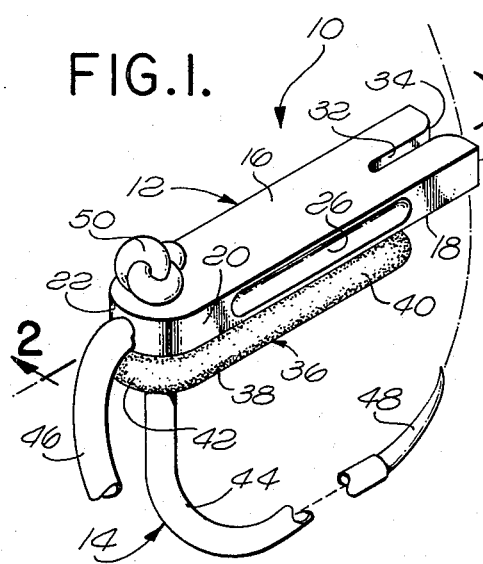
FIG. 1 is a perspective view of one form of a vessel occluding instrument constructed in accordance with the teachings of the present invention.

Referring to the drawing more particularly by reference numerals, the number 10 indicates one form of a novel vessel occluding instrument embodying the teachings of the present invention, which includes an elongated body member 12 with a longitudinally extending axis A, and a length of resilient tape 14.

The body member is made of a substantially rigid yet slightly resilient material, preferably plastic, and is elongated and generally rectangular in cross-section with top and bottom surfaces 16 and 18, respectively, opposed side walls 20, and first and second rounded ends 22 and 24, respectively.

Each of the side walls contains a longitudinally extending recess 26 which extends from adjacent the first end 22 to adjacent the second end 24.

A first passageway 28 extends through the body member between the top and bottom surfaces adjacent to the first end 22 substantially normal to the longitudinal axis A, and a second passageway 30 extends from the first end 22 and intersects the passageway at approximately a 90° angle, i.e. in general alignment with said longitudinal axis.

Extending inwardly from the second end 24 is a slot 32, the walls of which diverge outwardly adjacent the second end 24 to provide a throat 34 for a purpose to appear.

A relatively large resilient pad 36 is fastened to the bottom surface 18 by means of a suitable adhesive, the pad preferably being made from a soft rubber material and having a bottom surface, 38, opposed side surfaces 40, and opposed end surfaces 42 — all of which surfaces are roughened to reduce the degree of movement of a vessel being occluded. The width of the pad 36 is at least equal to and preferably slightly greater than the width of the body member 12, the length of the pad is at least equal to the distance between the end 22 and the inner end of the slot 32, and the side and end surfaces 40 and 42 are preferably rounded.

The resilient tape 14 is preferably of tubular construction and made from a conventional white silicone rubber. In the assembled instrument, the tape includes a first length 44 which extends downwardly from the body member, and a second length 46 which extends axially therefrom. Fastened to the free end of the first length 44 is a one-half circle blunt needle 48.

Figure 2:
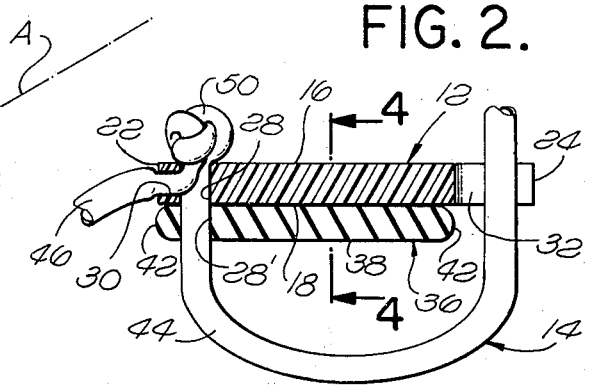
FIG. 2 is a vertical sectional view taken on the line 2—2 in FIG. 1, with the tape shown in elevation.
Figure 3:
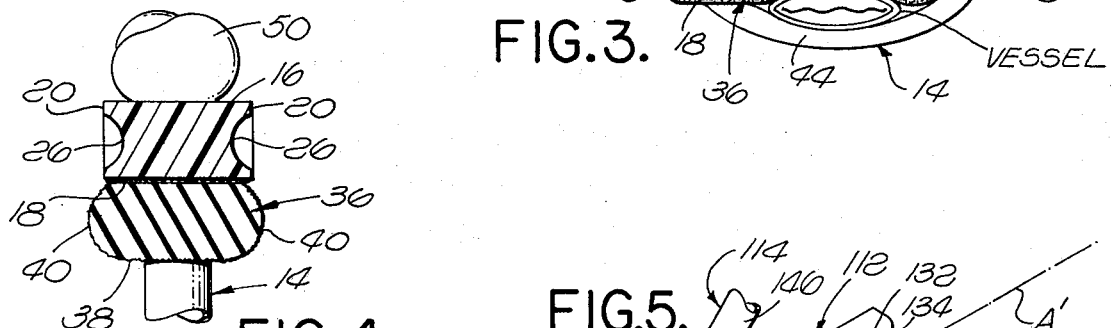
FIG. 3 is a side elevational view, taken from the same position as in FIG. 2 showing the instrument in vessel occluding position.
Figure 4:
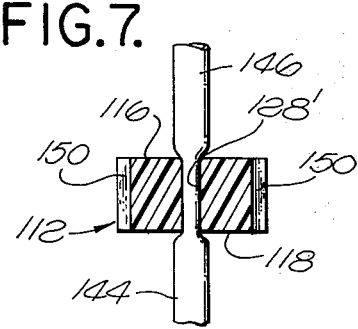
FIG. 4 is an enlarged, vertical sectional view taken on the line 4—4 in FIG. 2.

Referring to FIG. 2, the body member 12 can be fastened adjacent the center portion of the tape 14 by inserting the first length 44 through the passageway 30 and thence upwardly through the upper end of the passageway 28. After approximately one-half of the tape has been pulled through the aforementioned passageways, a simple knot 50 is tied in the tape, and the first length inserted downwardly through the passageway 28 and through an aligned similar passageway 28' contained in the pad 36, until the knot 50 is adjacent the upper surface 16 of the body member. The second length 46 is then pulled outwardly to draw the knot 50 tightly against said upper surface.

In use, after an incision has been made, the artery is identified and the blunt needle 48 carefully passed about the artery and pulled through, the first length 44 of the tape passing through the tissue without resistence. The needle may pass around both the coronary artery and its associated vein.

The tape is pulled through until the body member 12 approaches the coronary artery. A forceps is then used to grasp the body member at the grooves 26 to maintain it in position, and the first length 44 of the tape is pulled through the throat 34 and into the slot 32 in a holding relationship with the body member.

The artery is then entrapped and occluded between two resilient surfaces, i.e. the first length 44 of the tape and the bottom surface 38 of the resilient pad 36. The use of the two such resilient surfaces significantly diminishes the trauma usually associated with unyielding materials.

Also, the artery is occluded in an anterior posterior direction without significant distortion of the arterial wall, except at two points.

The novel vessel occluding instrument described herein can also be used for manipulating vessels, prior or subsequent to occlusion. Thus, by passing one end of the tape about the vessel, the vessel can be moved from side to side and elevated to provide an unobstructed view of the vessel without the necessity of pinching it between the fingers. Then, when it is desired to occlude the vessel, one end of the tape is pulled so as to move the body member 12 adjacent to the vessel, the body member is held in position with a forceps and the first length of the tape pulled through the throat 34 and into the opening 32, all as previously described.

It should also be noted that traction on the resilient tape can be increased to any desired level so that partial or total occlusion of a tubular structure such as a vessel, can be easily accomplished.

It is also significant that because of the manner in which the body member 12 is fastened to the tape 14, with the second length 46 of the tape extending from the end 22 of the body member substantially in axial alignment with the longitudinal axis A, the latter forms an obtuse angle with the first length 44 of the tape when the two free ends of the tape are grasped by the surgeon and pulled outwardly, as the first step in manipulating a vessel. Obviously, this reduces the angle of inclination between the tape and the body member, and thereby reduces the distance the end 24 extends away from the tape 14 during this maneuver.

Referring to FIGS. 5 through 8, the number 100 indicates a modified form of vessel occluding instrument embodying the teachings of the present invention, which is less expensive to produce than the embodiment previously described, but which is similar to it in many ways.

Thus, the modified instrument 100 includes the body member 112 and a length of resilient tape 114.

The body member is made of a substantially rigid yet slightly resilient material, preferably plastic, and is also elongated and generally rectangular in cross-section with a longitudinally extending axis A', top and bottom surfaces 116 and 118, respectively, opposed side walls 120, and first and second rounded ends 122 and 124, respectively.

In like manner, each of the side walls contains a longitudinally extending recess 126, and the body member contains a slot 132 with a throat 134 at the end 124.

As with the first embodiment, the modified vessel occluding instrument 100 includes a relatively large resilient pad 136 which is fastened to the bottom surface 118, and which includes a bottom surface 138, opposed side surfaces 140, and end surfaces 142 — all of which surfaces are preferably roughened, as previously described. Also, the width of the pad 136 is at least equal to the width of the body member, and extends from the end 122 to the inner end of the slot 132.

However, the modified instrument 100 differs from the first embodiment 10 in that instead of utilizing the right-angle passageways 28 and 30, there is provided a single passageway 128 at the end 122, which forms an acute angle with the top surface 116 and the longitudinally extending axis A', the lower end of the passageway 128 exiting from the bottom surface 118 at the edge of the end 122.

The resilient tape 114 is the same as previously described, i.e. of tubular construction and made from white silicone rubber.

To fasten the body member 112 to the tape 114, the latter is pulled through the passageway 128 — the tape and the passageway being of approximately the same size — until the body member is adjacent the center of the tape. The portion of the body member 112 adjacent the end 122 is then placed in a pressure applying device which engages the wide walls 120 adjacent the passageway 128, and moves them inwardly (FIG. 8) as indicated by the opposed arrows P, to form indentations 150, thereby causing the passageway 128 to be constricted or reduced in width as indicated by the number 128' in FIG. 7, so as to "crimp" or wedge the body member 112 onto the tape 114.

Figures 5, 6:
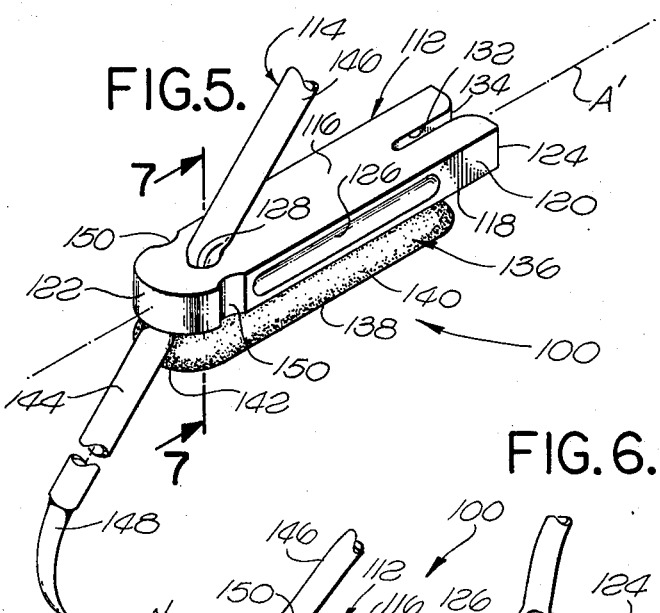
FIG. 5 is a perspective view similar to FIG. 1, showing a modified form of instrument.
FIG. 6 is a side elevational view of the vessel occluding instrument of FIG. 5, as it would appear during usage.
Figures 7, 8:
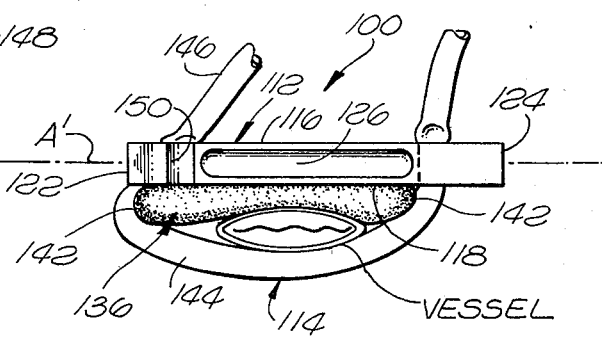
FIG. 7 is a vertical sectional view taken on the line 7—7 in FIG. 5.
FIG. 8 is a view similar to FIG. 7, schematically illustrating the diminsional relationship between the tape and the passageway prior to the "crimping" or pressure applying step.

This results in a first length 144 which extends in a downward direction and which has a one-half circle blunt needle 148 fastened to the free end thereof, and a second length 146 which extends in an upward direction from the upper surface 116 of the body member. As shown in FIGS. 5 and 6, the second length 146 of tape extends at an acute angle relatively to the upper surface 116 of the body member and the longitudinally extending axis A' thereof, whereby the distance the body member projects relative to the tape is restricted when the ends of the tape are grasped by a surgeon, in the same manner as previously described with the first embodiment Thus, it is apparent that there have been provided two embodiments of a novel vessel occluding instrument which fullfill all of the objects and advantages sought therefor.

I claim:

1. A vessel occluding instrument which includes an elongated body member having top and bottom surfaces, opposed sides, and first and second opposed ends; a first length of resilient tape extending from adjacent the first end of said body member; and means at the second end for releasably holding said first length of tape in a selected adjusted position relative to said bottom surface said bottom surface including
resilient pad means secured to the bottom surface of the body member extending from substantially one side to the other side, and from the first end to adjacent the holding means at the second end providing opposed resilient occluding means.

2. A vessel occluding instrument according to claim 1, in which the ends and sides of the resilient pad means are of arcuate configuration.

3. A vessel occluding instrument according to claim 1, in which the exposed surfaces of the resilient pad means are roughened.

4. A vessel occluding instrument according to claim 1, in which the body member has a longitudinally-extending axis, the first length of the tape extends from the bottom surface of the body member adjacent the first end, and which further includes a second length of resilient tape which extends from the first end substantially parallel with the longitudinally extending axis.

5. A vessel occluding instrument according to claim 4, in which the first length of tape is received in a first passageway which extends between the top and bottom surfaces of the body member, and the second length of tape is received in a passageway which extends from said first end to the first passageway.

6. A vessel occluding instrument according to claim 5, in which the first and second lengths of tape are continuous and included a knotted portion in contact with the top surface of the body at the first passageway.

7. A vessel occluding instrument according to claim 1, in which the first length of tape extends from the bottom surface at an obtuse angle, and which includes a second length of tape which extends from the top surface at an acute angle relative thereto.

8. A vessel occluding instrument according to claim 7, in which the first and second lengths of tape are continuous and are received in a passageway which extends through said first end of the body member at an acute angle relative to the top surface thereof.

9. A vessel occluding instrument according to claim 8, in which one end of the passageway is contiguous with the edge formed between said first end and the bottom surface.

10. A vessel occluding instrument according to claim 8, in which this tape and the passageway are generally of the same size, and a portion of the passageway is constricted after the tape is received therein, whereby the tape is wedged in a selected position in the passageway.

* * * * *